United States Patent [19]

Iwata

[11] Patent Number: 4,972,713
[45] Date of Patent: Nov. 27, 1990

[54] SENSOR OF THE THEFT AND THE LIKE OF AUTOMOBILES

[75] Inventor: Keisuke Iwata, Tokyo, Japan

[73] Assignee: Kabushiki Kaisha Iwata Electric, Tokyo, Japan

[21] Appl. No.: 359,049

[22] Filed: May 30, 1989

[30] Foreign Application Priority Data

Mar. 8, 1989 [JP] Japan ................................ 1-26532[U]

[51] Int. Cl.$^5$ .................................................. G01P 15/08
[52] U.S. Cl. ................................ 73/517 R; 310/329; 340/429
[58] Field of Search ............ 73/517 R; 340/426, 643, 340/566, 467, 429, 669; 310/329

[56] References Cited

U.S. PATENT DOCUMENTS

| | | | |
|---|---|---|---|
| 3,206,980 | 9/1965 | Nelson | 73/775 X |
| 4,051,395 | 9/1977 | Taylor | 310/329 |
| 4,395,908 | 8/1983 | Shopland | 310/329 X |
| 4,712,098 | 12/1987 | Laing | 310/329 X |
| 4,732,041 | 3/1988 | Iwata | 73/654 |
| 4,749,056 | 6/1988 | Iwata | 180/287 |

Primary Examiner—Jerry W. Myracle
Attorney, Agent, or Firm—Bauer & Schaffer

[57] ABSTRACT

A piezo-electric film is pasted to one surface of an elastic film fixed at the ends and a weight is attached substantially to the middle of the other surface of this elastic film.

5 Claims, 2 Drawing Sheets

SENSOR OF THE THEFT AND THE LIKE OF AUTOMOBILES

FIELD OF THE INVENTION

This invention relates to a sensor of the theft and the like of an automobile fitted in such proper space as within the engine compartment, chassis, passenger compartment, center pillar or trunk of an automobile to generate a signal by sensing such vibration as at the time of the theft of the automobile, that is, the vibration of the automobile artificially applied by the intrusion into the automobile compartment from outside, removal of the tire, breaking of the window glass and insertion of the key into the key hole of the door or trunk and to thereby prevent the theft and the like of the automobile as combined with any alarm and the like.

BACKGROUND OF THE INVENTION

There have been already provided such sensors of the theft and the like of automobiles as a sensor 1 utilizing the resonance of a vibrating plate of a hat-like cross-section as shown in FIG. 4, a sensor 2 utilizing the resonance of a disk-like vibrating plate fixed on the outer periphery as shown in FIG. 5 and a sensor 3 utilizing an electromagnetic induction as shown in FIG. 6.

In FIG. 4 showing the sensor 1, the reference numeral 4 represents a housing, 5 represents such rigid vibrating plate as a metal plate of a hat-like cross-section with both feet fixed to the housing 4, 6 represents a piezo-electric element pasted to the vibrating plate 5 and 7 and 8 represent lead wires for taking out the output signals of the piezo-electric element 6. This sensor 1 is fitted in such proper space as within the passenger compartment of an automobile so that the vibrating plate 5 may vibrate with the rocking of the automobile at the time of the theft, the vibration may be converted to an electric signal by the piezo-electric element 6, the signal may be output from between the lead wires 7 and 8 and the theft and the like may be thereby sensed.

However, in this sensor 1, as the above mentioned vibrating plate 5 is used, there has been a defect that the resonant sharpness is so large that, in case specific conditions are not met at the time of the theft, for example, in case the kind and loaded weight of the automobile are different, the theft and the like of the automobile will not be able to be positively sensed. As the rocking of the car body by the loaded body weight of the intruder into the passenger compartment vibrates at such low frequency as generally mostly below several 10 $H_z$, there has been also a defect that, in order to sense the vibration of this low frequency, the above mentioned sensor 1 must be formed to be large in the structure of the vibrating plate 5 and can not be made small.

In FIG. 5 showing the sensor 2, the reference numeral 9 represents a housing, 10 represents such rigid vibrating plate as a disk-like metal plate fixed on the outer periphery to the housing 9, 11 represents a piezo-electric element pasted to this vibrating plate 10 and 12 and 13 represent lead wires for taking out the output signals of the piezo-electric element 11. The same as the above mentioned sensor 1, this sensor 2 is fitted in such proper space as within the passenger compartment of an automobile so that the vibrating plate may vibrate with the rocking of the automobile at the time of the theft, this vibration may be converted to an electric signal by the piezo-electric element 11, this signal may be output from between the lead wires 7 and 8 and the theft or the like of the automobile may be thereby sensed.

However, even in this sensor 2, the same as in the above mentioned sensor 1, there has been a defect that, in order to sense a low frequency vibration, the sensor 2 must be formed to be large in the structure of the vibrating plate 10 and can not be made small.

Further, in FIG. 6 showing the sensor 3, the reference numeral 14 represents a housing, 15 represents an elastic string provided as stretched in this housing 14 and 16 represents a weight provided in the middle of this elastic string and formed of a permanent magnet 17 exposed on the lower surface. Also, a copper wire coil 18 is provided below the above mentioned weight 16. This sensor 3 is fitted in a proper space of an automobile. The principle of the vibration of this sensor 3 is of a torsion bar system with the elastic string 15 as an axis so that, when the automobile is vibrated, the weight 16 will swing as a pendulum with the elastic string 15 as an axis, the magnetic flux intersecting the copper wire coil 18 by the permanent magnet 17 of the weight 16 will vary, an induction current will be generated in this copper wire coil 18 and the theft and the like of the automobile will be thereby sensed.

However, in the above mentioned sensor 3, there has been a defect that, when the plane in which the above mentioned copper wire coil 18 is arranged inclines much as in the case that the car body inclines much while parked, the weight 16 will rotate to be directed in the perpendicular direction by the gravity, the permanent magnet 17 of the weight 16 will separate away from the copper wire coil 18 and the sensitivity will be thereby reduced. There has been also a defect that, in case the car is parked above high voltage lines embedded under the ground or in case there is in the vicinity a transmitting antenna generating strong electromagnetic waves, under the influence of the electromagnetic induction from outside, an induction current will be generated in the above mentioned copper wire coil 18 and a mis-operation or operation failure by an excess input will be caused.

Also, as a sensor of the theft and the like of an automobile, there has been provided a sensor provided with a vibration converting part for converting the vibration of the car body to an electric signal of a frequency coinciding with the frequency of this vibration over a wide frequency band without utilizing the resonance.

However, in this sensor, a filter has been indispensable to prevent a mis-operation from being caused by an external acoustic noise or meteorological factor. That is to say, as the above mentioned vibration converting part converts to an electric signal not only the vibration of the car body of a low frequency generated at the time of the theft or the like but also the vibration of the car body of a comparatively high frequency based on such external sound as of a klaxson of another car, siren of an emergency car, rainfall or wind or on a meterological factor, a filter for taking only the signal based on the vibration of the car body of a low frequency generated at the time of the theft out of the electric signals has been indispensable to the above mentioned sensor.

SUMMARY OF THE INVENTION

This invention is to provide a sensor of the theft and the like of an automobile wherein the theft and the like of an automobile can be positively sensed, a mis-operation by an external acoustic noise or the like can be prevented without requiring a filter, even if the car body inclines much while parked, the sensitivity will not substantially reduce, a mis-operation under the influence of an electromagnetic induction from outside or an operation failure by an excess input is not likely to occur, the contour can be made small and the formation is simple and cheap.

Therefor, in this invention, a piezo-electric film is pasted to one surface of an elastic film fixed at the ends and a weight is attached substantially to the middle of the other surface of this elastic film.

The sensor according to the present invention is fitted in a proper space of an automobile. Therefore, in the present invention, as the weight is attached substantially to the middle of the elastic film fixed at the ends, when the car body vibrates, the above mentioned elastic film will be vibrated by the operation of the above mentioned elastic film and weight. As a piezo-electric film is pasted to the elastic film, with the vibration of the elastic film, a mechanical extending and contracting force will be applied to the piezo-electric film and an electric signal as a sensing signal will be obtained from this piezo-electric film.

In the present invention, as the resonant frequency of the above mentioned elastic film is determined by the mass of the weight and the tension and size of the elastic film, by properly selecting them, the resonant frequency of the elastic film can be made a low frequency below several 10 $H_z$. Also, in the present invention, as the elastic film is used instead of such rigid vibrating plate as a metal plate, the resonant sharpness will be comparatively small. Therefore, according to the present invention, when a vibration of a frequency in a comparatively wide range of a frequency band below several 10 $H_z$ is produced in an automobile, a comparatively large signal will be able to be obtained from the piezo-electric film.

Therefore, according to the present invention, as a low frequency vibration of an automobile is detected, there can be obtained an advantage that no mis-operation will be made by an external unnecessary acoutic noise or the like. As the resonant sharpness is smaller and a vibration in a comparatively wider range can be sensed than in a conventional sensor using a vibrating plate, there can be obtained an advantage that, even if the kind and loaded weight of the automobile are different, the theft and the like will be able to be positively sensed. Further, as a comparatively large signal will be obtained from the piezo-electric film when a low frequency vibration is produced in the automobile, no filter is required and there can be obtained an advantage that the sensor can be provided at a low cost.

Also, according to the present invention, as the mass of the weight acts to reduce the resonant frequency of the elastic film in reducing the resonant frequency of the elastic film to a low frequency as described above, the resonant frequency can be set at a low frequency without making the elastic film large and therefore there can be obtained an advantage that the contour of the sensor can be made small.

Further, according to the present invention, even if the car body inclines much while parked and the plane of the above mentioned elastic film inclines much to the horizontal plane, the sensitivity will reduce only in proportion to the cosine (cos $\theta$) of the inclination angle $\theta$ and therefore there can be obtained an advantage that the sensitivity will not substantially reduce.

Also, according to the present invention, as a piezo-electric film is used but no copper wire coil is used, there can be obtained an advantage that a mis-operation under the influence of an electromagnetic induction from outside by high voltage lines embedded under the ground or transmitting antennae transmitting strong electromagnetic waves and an operation failure by an excess input are not likely to occur.

Further, as the sensor of the present invention is formed of an elastic film, piezo-electric film and weight, there can be obtained an advantage that the structure is simple and can be provided at a low cost.

DETAILED DESCRIPTION OF THE INVENTION

Figure 1:
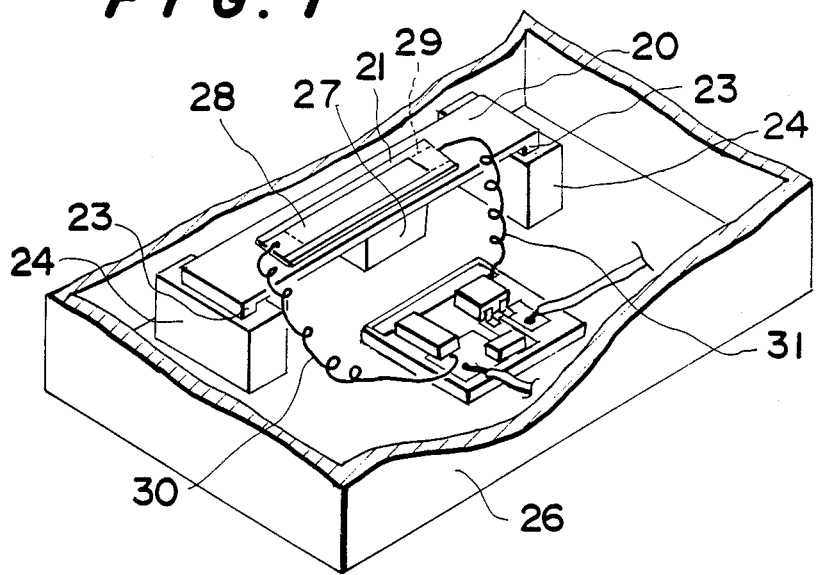
FIG. 1 is a perspective view showing an essential part of a sensor of the theft and the like of an automobile embodying the present invention.

The present invention shall be explained in the following on the basis of the embodiment shown in the drawings.

Figure 2:
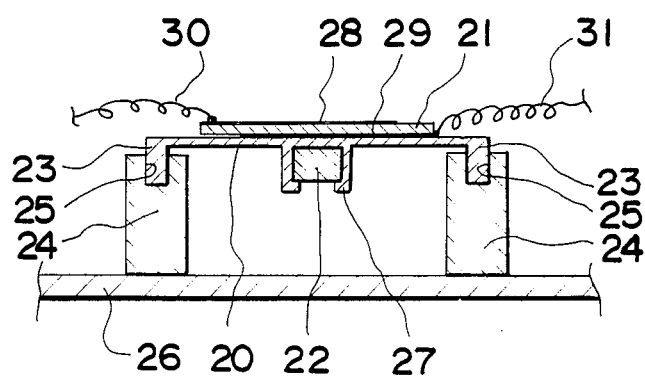
FIG. 2 is a vertically sectioned view of the same.

FIG. 1 is a perspective view showing an essential part of a sensor of the theft and the like of an automobile according to the present invention. FIG. 2 is a vertically sectioned view of the same.

In FIGS. 1 and 2, the reference numeral 20 represents an elastic film fixed at the ends, a piezo-electric film 21 is pasted to one surface of this elastic film 20 and a weight 22 is attached substantially to the middle of the other surface of the elastic film 20.

The above mentioned elastic film 20 may be made of any material but preferably of a silicone rubber little in the variation with the lapse of years.

In the embodiment shown in the drawings, the above mentioned elastic film 20 is formed to be rectangular and has stoppers 23 formed integrally at both ends, fitted in grooves 25 in supporting stands 24 and bonded with a bonding agent or the like. Needless to say, the elastic film 20 may be fixed at the ends by any other method. For example, the elastic film 20 may be fixed at the ends directly to the tips of the supporting stands 24 by being bonded with a bonding agent or the like without forming the above mentioned stoppers 23 or may be fixed with pressing plates and rivets. The contour of the elastic film 20 is not limited to be rectangular but may be made, for example, circular and may be fixed on the periphery.

By the way, though not illustrated in detail in the drawings, the supporting stands 24 are housed together with the other component parts in a box-like housing 26 and are fixed to the housing 26. Needless to say, without providing the supporting stands 24, the elastic film 20 may be fixed at the ends directly to the wall surfaces of the housing 26.

In the illustrated embodiment, the weight 22 is attached to the elastic film 20 by being contained in a bag 27 molded integrally with the elastic film 20. Needless to say, the weight 22 attaching method is not limited to this but, for example, the weight 22 may be bonded to the elastic film 20 with a bonding agent or the like. Also, in the illustrated embodiment, the contour of the weight 22 is made cubic but is not limited to be so and may be, for example, columnar. Further, the material of the weight 22 is not particularly limited but it is desirable to form the weight 22 by using such material of a large specific gravity as lead.

The piezo-electric film 21 may be any film but may be preferably such soft film as, for example, of PVDF (polyvinylidene fluoride) or such high molecular weight piezo-electric film as of PECM because, even when subjected to a strong mechanical shock, it will not be likely to be broken. The thickness of the piezo-electric film 21 is not particularly limited but may be, for example, about 10 μm.

By the way, the piezo-electric film 21 has on both surfaces electrode parts 28 and 29 to which lead wires 30 and 31 are respectively connected.

According to the present invention of the above mentioned structure, the housing 26 is fitted directly or by using other metal pieces or the like in such proper space as within the engine compartment, chassis, passenger compartment, center pillar or trunk of an automobile. Therefore, when the car body vibrates, the vibration will be transmitted to the elastic film 20 through the housing 26 and supporting stands 24 and the elastic film 20 will be vibrated by the operation of the elastic film 20 and weight 22. As the piezo-electric film 21 is pasted to the elastic film 20, a mechanical extending and contracting force will be applied to the piezo-electric film 21 with the vibration of the elastic film 20 and an electric signal as a sensing signal will be obtained between the lead wires 30 and 31.

In the illustrated embodiment, as the elastic film 20 is formed to be rectangular and is fixed at both ends, if the mass of the weight 22 is represented by m, the length between both ends of the elastic film 20 is represented by l, the tension of the elastic film 20 is represented by T and the constant is represented by k, the resonant frequency $f_r$ of the above mentioned elastic film 20 will be:

$$f_r = k \sqrt{T/lm}$$

After all, as the resonant frequency $f_r$ of the elastic film 20 is determined by the mass of the weight 22, the length between both ends of the elastic film 20 and its tension, by properly selecting them, the resonant frequency of the elastic film 20 can be made below several 10 $H_z$. Therefore, according to the present invention, when a vibration of a frequency in a comparatively wide range among frequencies below several 10 $H_z$ is produced in an automobile, a comparatively large signal will be able to be obtained from the piezo-electric film 21.

Therefore, according to the present invention, as the low frequency vibration of the automobile is detected, there can be obtained an advantage that no mis-operation will be made by an external unnecessary acoustic noise or the like. Also, as a vibration of a smaller resonant sharpness and in a comparatively wider range than in a conventional sensor using a vibrating plate can be sensed, there can be obtained an advantage that, even if the kind and loaded weight of the automobile are different, the theft and the like will be able to be positively sensed. Further, when a low frequency vibration is produced in the automobile, a comparatively large signal will be obtained from the piezo-electric film 21 and therefore there can be obtained an advantage that no filter is required and the sensor can be provided cheaply.

By the way, it has been confirmed by the experiments made by the present inventor that it is desirable to set the resonant frequency of the above mentioned elastic film 20 at about 15 to 30 $H_z$.

Also, according to the present invention, when the resonant frequency of the elastic film 20 is made a low frequency as described above, as understood from the above formula, the mass of the weight 22 will act to reduce the resonant frequency of the elastic film 20, therefore the resonant frequency can be set at a low frequency without making the elastic film 20 large and there can be obtained an advantage that the contour of the sensor can be made small.

Further, according to the present invention, even if the car body inclines much while parked and the plane of the above mentioned elastic film 20 inclines much to the horizontal plane, the sensitivity will reduce only in proportion to the cosine (cos θ) of the inclination angle and therefore there can be obtained an advantage that the sensitivity will not substantially reduce. Therefore, there can be obtained an advantage that, if the sensor of the present invention is fitted to an automobile so that the plane of the elastic film 20 may be substantially horizontal, there will be no need of being nervous to make the plane of the elastic film 20 perfectly horizontal when fitted.

Further, in the present invention, as the piezo-electric film 21 is used but no copper wire coil is used, there can be obtained an advantage that a mis-operation under the influence of an electromagnetic induction from outside by high voltage lines embedded under the ground or transmitting antennae transmitting strong electromagnetic waves and an operation failure by an excess input are not likely to occur.

By the way, according to the present invention, as described above, as an electric signal as a sensing signal of the theft and the like of an automobile is obtained between the lead wires 30 and 31, by properly processing this signal with a separately provided electric circuit, for example, an electric circuit connecting an amplifier, detector, holding circuit, relay driving circuit and relay in the order mentioned, there can be formed a crime preventing alarm apparatus or the like wherein such abnormal situation as when the tire to be stolen is jacked up, the body weight is loaded at the time of the intrusion into the car, the window glass is broken, the key is inserted into the key hole of the door or trunk or the parked car is struck from behind or is tugged can be made known to the owner or the like by sounding a buzzer or emitting a wireless electric wave signal.

Figure 3:
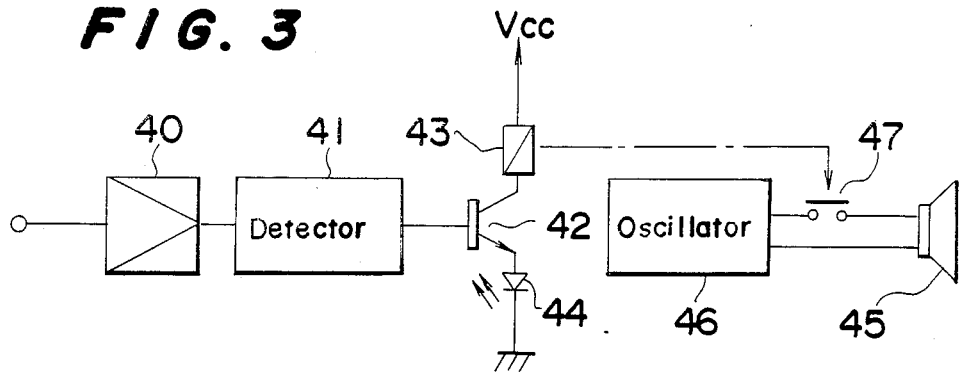
FIG. 3 is an electric circuit diagram showing an example of an outside circuit.
Figure 4:
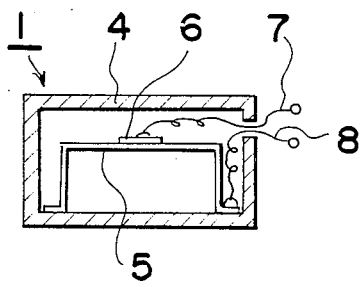
FIG. 4 is a vertically sectioned view showing a conventional sensor of the theft and the like of an automobile.
Figure 5:
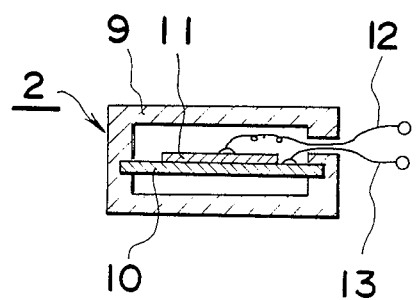
FIG. 5 is a vertically sectioned view showing another conventional sensor of the theft and the like of an automobile.
Figure 6:
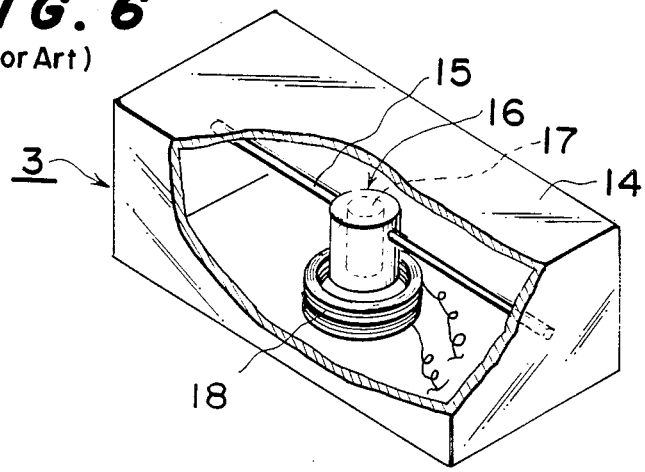
FIG. 6 is a partly sectioned perspective view showing further another conventional sensor of the theft and the like of an automobile.

An example of an outside circuit connected to the sensor of the present invention is shown in FIG. 3.

In FIG. 3, the reference numeral 40 represents an amplifier to which the above mentioned lead wires 30 and 31 are connected and into which the output signal of the piezo-electric film 21 is input, 41 represents a detector receiving the output signal of this amplifier, convering the signal above a predetermined level to a direct current voltage signal and outputting it and 42 represents a switching transistor in which the output signal of this detector 41 is input into the base. The collector of this switching transistor 42 is connected to a direct current source $V_{cc}$ through a coil part 43 of a relay and the emitter is earthed through a light emitting diode 44. Further, the reference numeral 45 represents a speaker, 46 represents an oscillator generating an alarming sound by driving this speaker 45 and 47 represents a contact of the above mentioned relay and conducting when a voltage is applied to the above mentioned coil part 43. By the way, the above mentioned light emitting diode 44 will be utilized in the case of adjusting the amplitude of the amplifier 40 and adjusting the detecting level of the detector 41.

According to this outside circuit, when a sensing signal is obtained from the sensor of the present invention, the above mentioned switching transistor 42 will conduct, a voltage will be applied to the coil part 43 of the relay, the contact 47 will conduct and an alarming sound will be generated from the speaker 45.

Needless to say, the outside circuit connected to the sensor of the present invention is not limited to the above mentioned formation shown in FIG. 3 but may be of any other formation.

By the way, in the illustrated embodiment, as shown in FIG. 1, a part of the above mentioned outside circuit is also contained within the housing 26.

As described in detail in the above, according to the present invention, there can be obtained effects that the theft and the like of an automobile can be positively sensed, a mis-operation by an external acoustic noise or the like can be prevented without requiring a filter, the sensitivity will not substantially reduce even if the car body inclines much while parked, a mis-operation under the influence of a magnetic induction from outside and an operation failure by an excess input are not likely to occur, the contour of the sensor can be made small and the formation is simple and cheap.

What is claimed is:

1. A vehicular anti-theft sensor comprising a resonant piezoelectric film bonded to one surface of an elongated elastic carrier film for conjoint vibration, said carrier film being supported at its end in a substantially horizontal position and being provided with a weight attached substantially midway, its ends on its other surface whereby changes in vibration of said vehicle modifies the response of said piezoelectric film to produce an output signal reflective therof.

2. A vehicular anti-theft sensor comprising an elongated thin elastic carrier film, means for mounting said carrier film under tension on said vehicle to vibrate in response to movement on said vehicle, a weight secured to the underside of said carrier film to regulate the frequency of the vibration, and a resonant piezoelectric film bonded to the upper surface of said carrier film for conjoint vibration therewith, the resonance of said piezoelectric film being modified by the conjoint vibration to produce an output signal reflective thereof.

3. A vehicular anti-theft sensor according to claim 2 including an enclosure for said carrier film and piezoelectric film, said carrier having a bottom wall and means for securing said enclosure to said vehicle, a pair of spaced supports fixed on said bottom wall and means for securing the ends of said carrier film to respective supports.

4. The vehicular anti-theft sensor according to claim 3, wherein said carrier film is secured at its ends to a respective one of said supports.

5. The vehicular anti-theft sensor according to claim 4, wherein the ends of said carrier film are provided with depending flanges and the supports are provided with receiving grooves for said flange, said sensor including means for securing said flanges in said grooves.

* * * * *

UNITED STATES PATENT AND TRADEMARK OFFICE
CERTIFICATE OF CORRECTION

PATENT NO. : 4,972,713

DATED : November 27, 1990

INVENTOR(S) : KEISUKE IWATA

It is certified that error appears in the above-identified patent and that said Letters Patent is hereby corrected as shown below:

Column 8, line 9, "response" should be --resonance--

Signed and Sealed this

Twenty-eighth Day of April, 1992

Attest:

HARRY F. MANBECK, JR.

*Attesting Officer*      *Commissioner of Patents and Trademarks*